(12) United States Patent
Yano

(10) Patent No.: US 6,851,299 B2
(45) Date of Patent: Feb. 8, 2005

(54) MEASURING APPARATUS OF COMPONENT CONTAINED IN TEST WATER

(75) Inventor: Kenkichi Yano, Ryugasaki (JP)

(73) Assignee: Seishin Engineering Co., Ltd., Tokyo (JP)

(*) Notice: Subject to any disclaimer, the term of this patent is extended or adjusted under 35 U.S.C. 154(b) by 122 days.

(21) Appl. No.: 10/294,169

(22) Filed: Nov. 14, 2002

(65) Prior Publication Data

US 2003/0101802 A1 Jun. 5, 2003

(30) Foreign Application Priority Data

Dec. 4, 2001 (JP) ......................................... 2001-370501

(51) Int. Cl.[7] .............................................. G01N 33/00
(52) U.S. Cl. ...................... 73/61.41; 73/61.55; 250/425
(58) Field of Search .............................. 73/61.41, 61.55, 73/61.59, 23.41, 23.42, 863.11, 864.21, 864.81; 250/425; 422/80; 436/146

(56) References Cited

U.S. PATENT DOCUMENTS

| | | | | |
|---|---|---|---|---|
| 3,864,088 A | * | 2/1975 | Delin et al. ................ | 422/80 |
| 4,095,951 A | * | 6/1978 | DiCola et al. .............. | 422/80 |
| 4,940,667 A | * | 7/1990 | Goldstein et al. ........... | 436/157 |
| 5,328,663 A | * | 7/1994 | Ligon, Jr. .................. | 422/78 |
| 5,873,980 A | * | 2/1999 | Young et al. ................ | 203/1 |

FOREIGN PATENT DOCUMENTS

| | | | | |
|---|---|---|---|---|
| JP | 56050102 A | * | 5/1981 | ............. C01B/3/26 |
| JP | 5-18918 | | 1/1993 | |
| JP | 8-304376 | | 11/1996 | |
| JP | 10-153593 | | 6/1998 | |
| JP | 10-160701 | | 6/1998 | |
| JP | 2000-121628 | | 4/2000 | |

* cited by examiner

Primary Examiner—Charles D. Garber
(74) Attorney, Agent, or Firm—Jordan and Hamburg LLP

(57) ABSTRACT

A measuring apparatus of a component contained in test water according to the invention can prevent a test water feed nozzle from clogging up and smoothly feed air into a combustion furnace, and further, can accurately measure in a short time carbon dioxide gas obtained from the complete combustion of an inorganic substance contained in test water. In a test water dropping unit 20 of the measuring apparatus 10, a test water dropping nozzle 21 for dropping test water into a combustion furnace 30 is provided at a top of the combustion furnace 30, and a protective pipe 23 in which this test water dropping nozzle 21 is accommodated is disposed outside the test water dropping nozzle 21. The bottom end 23a of the protective pipe 23 is extended downward from the test water dropping nozzle 21 and is formed at an acute angle, and the tip 21a of the test water dropping nozzle 21 is disposed in abutment with the inner circumferential surface 24 of the protective pipe 23.

5 Claims, 5 Drawing Sheets

PRIOR ART

MEASURING APPARATUS OF COMPONENT CONTAINED IN TEST WATER

BACKGROUND OF THE INVENTION

1. Field of the Invention

The present invention relates to a measuring apparatus of a component contained in test water, which apparatus is used in the case of feeding test water accompanied by air, in the state of drops into a combustion furnace, combusting the fed test water in the combustion furnace, taking carbon dioxide gas generated from the combustion of the test water out of the combustion furnace, and measuring the numerical value of organic carbon (TOC), total carbon (TC) or the like.

2. Background Art

In a related-art carbon dioxide gas measuring apparatus 100 as shown in FIG. 5, test water is fed to a feed pipe 102 by a feed pump 101, and this test water is introduced into a feed nozzle 103. The test water is fed in the state of drops 106 into a combustion furnace 105 from a tip 103a of the feed nozzle 103.

The combustion furnace 105 is constructed so that a plurality of alumina balls 109 in a reactor 107 and a pipe 108 are heated by a heater 110, and the interior of the combustion furnace 105 is held at approximately 850° C. Accordingly, the drops 106 dropped into the interior of the pipe 108 of the combustion furnace 105 are reliably combusted, and a component such as carbon dioxide contained in the drops 106 is extracted in a gaseous state.

In the meantime, air (hereinafter referred to as "carrier air") is introduced into the combustion furnace 105 from an air feed pipe 113 via an air introducing pipe 114, and this carrier air is fed to the interior of the combustion furnace 105 from a tip 114a of the air introducing pipe 114 as indicated by arrows.

This carrier air has the purpose of transporting gases generated by the combustion of the drops 106 to the exterior of the combustion furnace 105 via a gas introducing pipe 115 as indicated by an arrow, and further has the purpose of feeding air for combustion.

The gases introduced into the gas introducing pipe 115 by this carrier air accompany the carrier gas and are introduced into an analyzer such as an infrared analyzer (not shown). In the analyzer, the concentration of a target gas contained in the gases is measured, and the measured result is outputted as a signal.

SUMMARY OF THE INVENTION

Since the feed nozzle 103 of test water is disposed in the combustion furnace 105 and is used under an atmosphere of high temperature, the feed nozzle 103 is generally formed of quartz glass superior in heat resistance so that the thermal deformation of the feed nozzle 103 is restrained by the quartz glass.

However, the feed nozzle 103 made of quartz glass is not sufficient in water repellency (i.e., drainage performance), and has the problem that if test water is combusted with test water adhering to the tip 103a of the feed nozzle 103, an evaporated residue contained in the test water easily adheres to the tip 103a of the feed nozzle 103 and clogs up the feed nozzle 103.

There is also a case where an hydrochloric acid atmosphere is formed in the combustion furnace 105 when hydrochloric acid is added to test water to remove inorganic carbon contained in the test water. In addition, the air introducing pipe 114 is disposed in a comparatively low temperature area of the combustion furnace 105 and tends to be cooled by air passing through the interior of the air introducing pipe 114, so that dew which contains hydrochloric acid easily adheres to a portion near the tip 114a of the air introducing pipe 114. Particularly in the case where the material of the air introducing pipe 114 is stainless steel, there occurs the problem that the corrosion of the air introducing pipe 114 is caused by the dew adhering to the tip 114a.

Furthermore, although test water is fed in the form of drops into the combustion furnace 105 from the feed nozzle 103 by the feed pump 101, the test water needs to pass through many portions where the test water is not accompanied by air, from the feed pump 101 to the tip 103a of the feed nozzle 103, so that there occurs the problem that a long time is taken to transport the test water from the feed pump 101 to the nozzle dropping port 103a (the related art apparatus takes a period of time 4–10 minutes longer than does a type according to the invention).

The invention aims to solve all the above-described problems by providing a measuring apparatus of a component contained in test water, which apparatus prevents a test water feed nozzle from clogging up and prevents corrosion of a portion near the tip of an air introducing pipe, and can also shorten the time required to transport test water from the position of a feed pump to a nozzle dropping port.

An aspect of the invention, therefore, provides a measuring apparatus of a component contained in test water, which feeds test water accompanied by air, into a combustion furnace in the state of drops, combusts the fed test water in the combustion furnace, takes gases generated from the combusted test water out of the combustion furnace and measures a component of the gas. The measuring apparatus includes a test water dropping nozzle disposed at a top of the combustion furnace for dropping the test water into the combustion furnace, and a protective pipe disposed outside the test water dropping nozzle. A tip of the protective pipe is extended downward from the test water dropping nozzle and is formed at an acute angle, and a tip of the test water dropping nozzle is disposed in abutment with an inner circumferential surface of the protective pipe.

In the measuring apparatus of a component contained in test water according to the invention, the protective pipe is disposed outside the test water dropping nozzle to protect the test water dropping nozzle, and the tip of the protective pipe is extended downward from the test water dropping nozzle and is disposed in abutment with the inner circumferential surface of the protective pipe.

Accordingly, the test water dropped from the tip of the test water dropping nozzle is introduced to the inner circumferential surface of the protective pipe, and the test water introduced to the inner circumferential surface is made to flow down to the tip of the protective pipe and is combusted while the test water is being dropped from the tip of the protective pipe into the combustion furnace. When the measuring apparatus is used for a long time, an evaporated residue generated from test water adheres to the periphery of the tip of the protective pipe. However, since the protective pipe is formed to be comparatively thick so that the test water dropping nozzle is accommodated in the protective pipe, the protective pipe is prevented from clogging up even if an evaporated residue generated from the test water due to the combustion thereof adheres to the tip of the protective pipe.

According to another aspect of the invention, in the measuring apparatus, a disk-shaped separating member for separating upper and lower portions of the combustion furnace from each other is fitted at a location near a bottom end of an outer circumferential wall of the protective pipe.

Because this separating member is fitted, a portion of lower temperature near the top of the combustion furnace is separated from a portion of higher temperature near the bottom of the combustion furnace, whereby temperature nonuniformity is reduced in the combustion furnace and the efficiency of combustion of test water is improved.

According to further aspect of the invention, in the measuring apparatus, the air is fed into the combustion furnace through the test water dropping nozzle.

Since the air is fed into the combustion furnace through the test water dropping nozzle, the test water within the test water dropping nozzle can be made to flow rapidly to the tip of the test water dropping nozzle by the air. Accordingly, the test water can be efficiently guided from the tip of the test water dropping nozzle to the inner circumferential surface of the protective pipe, and while the test water is being dropped into the combustion furnace, the test water can be dropped in the form of small drops.

Accordingly, the drops of the test water dropped in this manner can be efficiently completely combusted, whereby the amount of gas required to measure carbon dioxide gas in the test water can be obtained in a comparatively short time.

According to still further aspect of the invention, in the measuring apparatus, the test water dropping nozzle is formed of polytetrafluoroethylene and the protective pipe is formed of quartz glass.

The test water dropping nozzle is formed of polytetrafluoroethylene superior in water repellency, and can reliably drain test water off the tip of the test water dropping nozzle to prevent test water from easily adhering to the tip of the test water dropping nozzle.

Accordingly, while the drops of test water are being combusted, an evaporated residue is prevented from adhering to the tip of the test water dropping nozzle, whereby the tip of the test water dropping nozzle can be prevented from being clogged up.

In addition, since the protective pipe is formed of quartz glass superior in heat resistance, even if the protective pipe is heated at high temperatures in the combustion furnace, for example, the tip of the protective pipe is prevented from being melted by heat, whereby test water can be efficiently dropped from the tip of the protective pipe. Accordingly, test water can be efficiently fed into the combustion furnace.

According to yet further aspect of the invention, in the measuring apparatus, a zero water feed pipe for feeding zero water to the test water dropping nozzle communicates with the test water feed pipe for feeding the test water.

In the measuring apparatus, zero water needs to be fed to the test water dropping nozzle or the protective pipe so that the protective pipe are cleaned or zero-point adjustment (initial-value setting) is performed on the measuring apparatus. In the related art, the test water feed pipe for feeding test water is also used as means for feeding zero water, but if the test water feed pipe is used, zero water needs to flow through the entire test water feed pipe, so that zero water flows through a flow passage longer than necessary.

As a result, it takes time to clean the test water dropping nozzle and the protective pipe and to adjust the zero point (set the initial values) of the measuring apparatus of a component.

To cope with this problem, in this aspect of the invention, the measuring apparatus is constructed so that the zero water feed pipe communicates with the test water feed pipe. Since a dedicated flow passage through which zero water is made to flow can be obtained, the length of the zero water feed pipe can be made short, and it is possible to shorten the time required to clean the test water dropping nozzle and the protective pipe and the time required for the zero-point adjustment (initial-value setting) of the measuring apparatus.

BRIEF DESCRIPTION OF THE DRAWINGS

The invention will become more readily appreciated and understood from the following detailed description of preferred embodiments of the invention when taken in conjunction with the accompanying drawings, in which.

DETAILED DESCRIPTION OF THE INVENTION

Preferred embodiments of a measuring apparatus of a component contained in test water according to the invention will be described below in detail with reference to the accompanying drawings.

Figure 1:
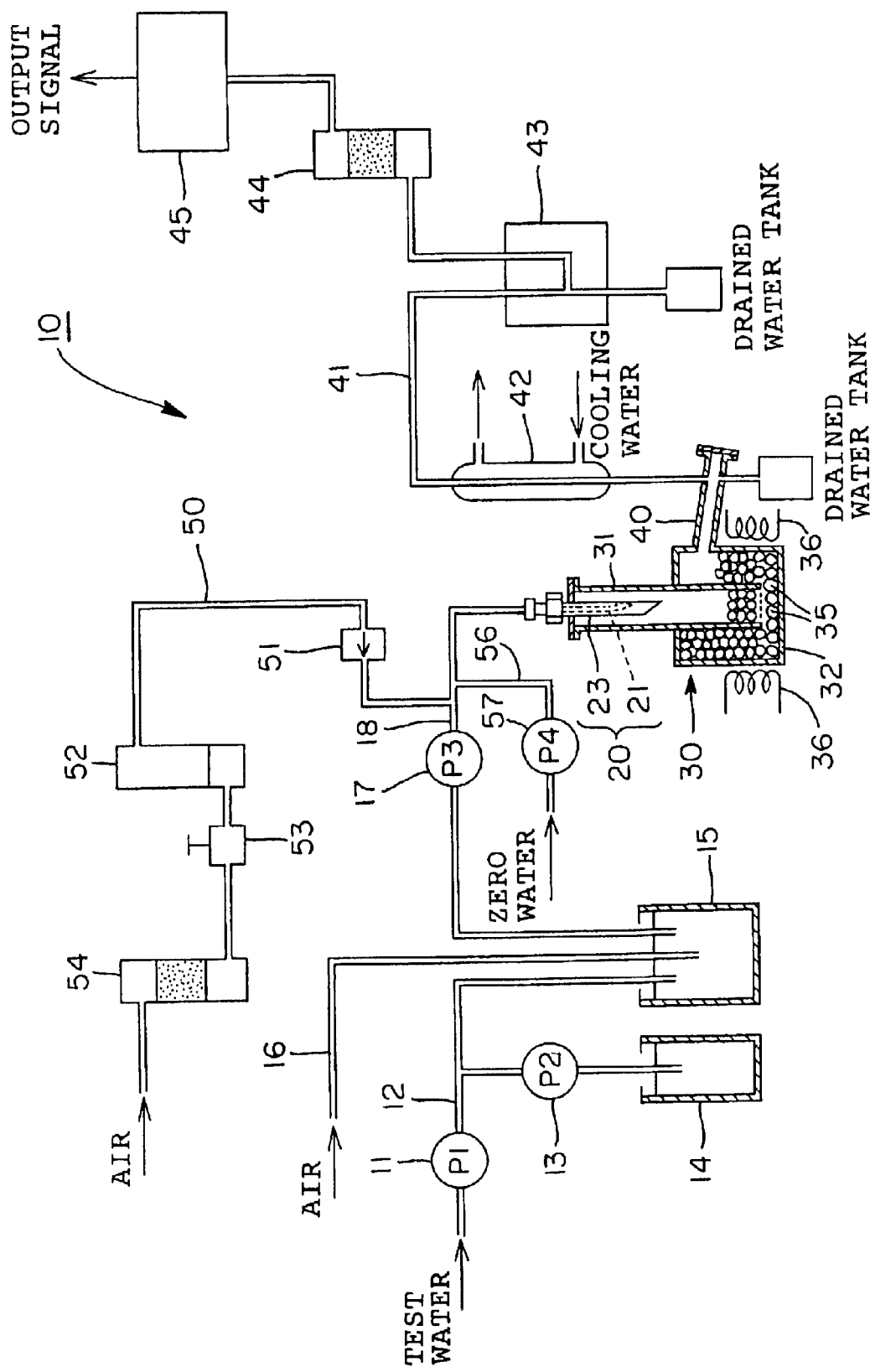
FIG. 1 is a general schematic view of a measuring apparatus of a component contained in test water according to the invention.
Figure 2:
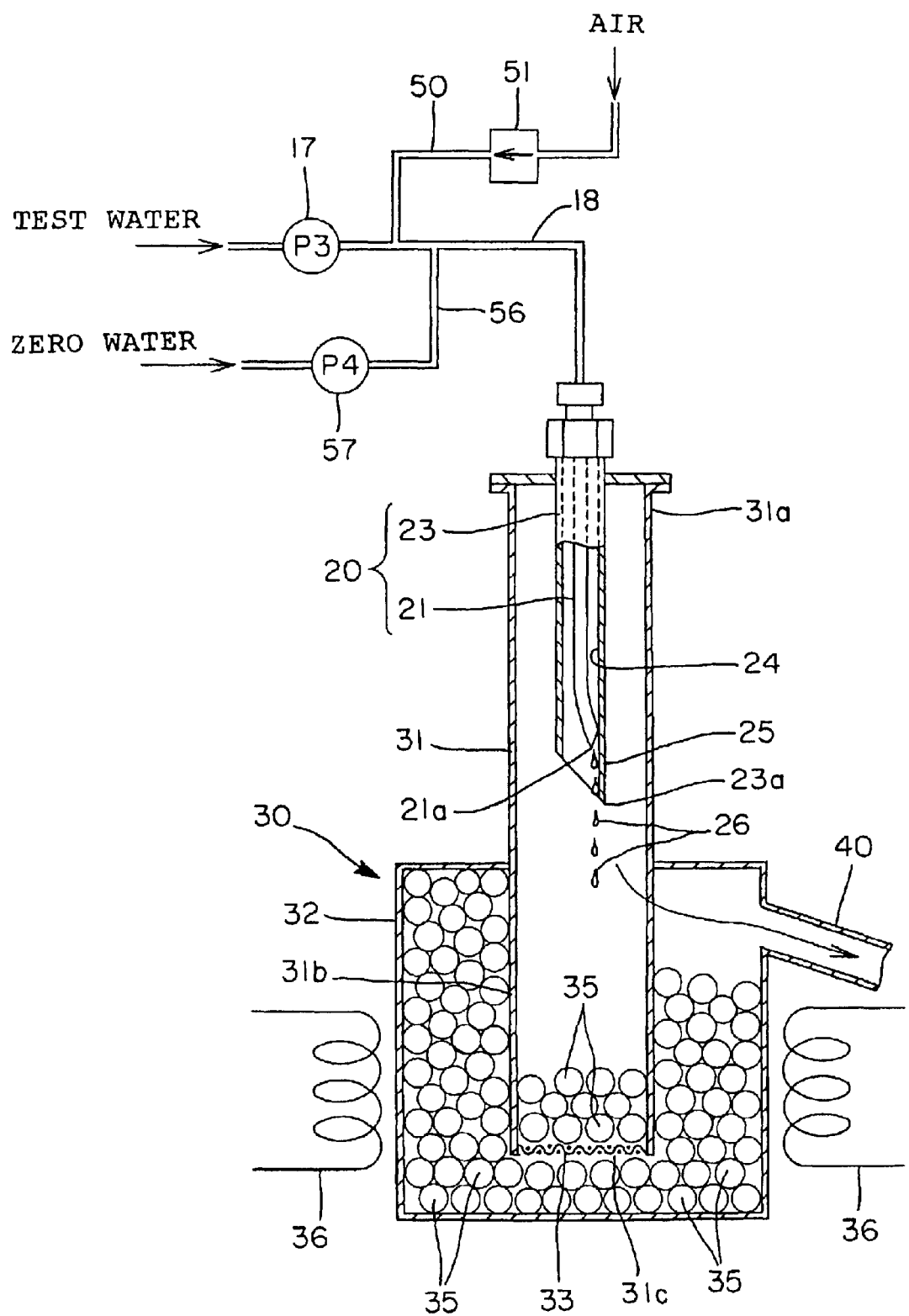
FIG. 2 is a vertical sectional view of a combustion furnace and a test water dropping unit of the measuring apparatus.
Figure 3:
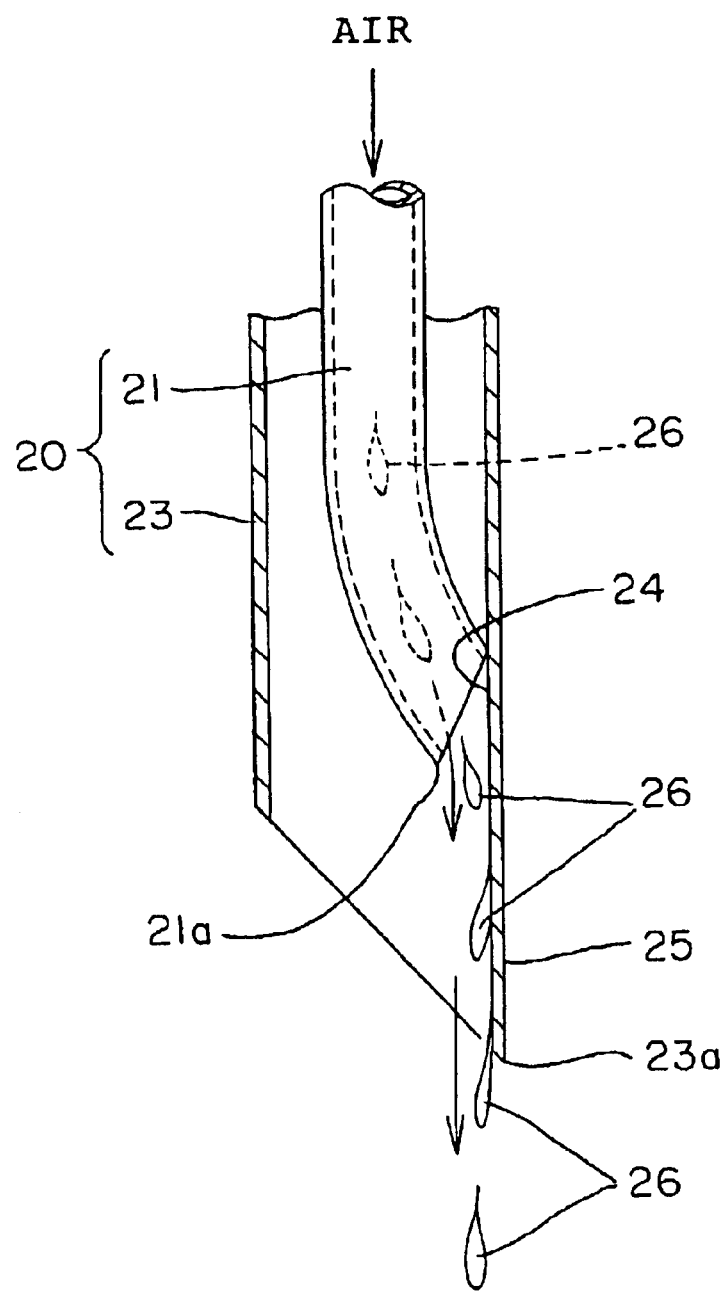
FIG. 3 is a vertical sectional view of the essential portion of the measuring apparatus.
Figure 4:
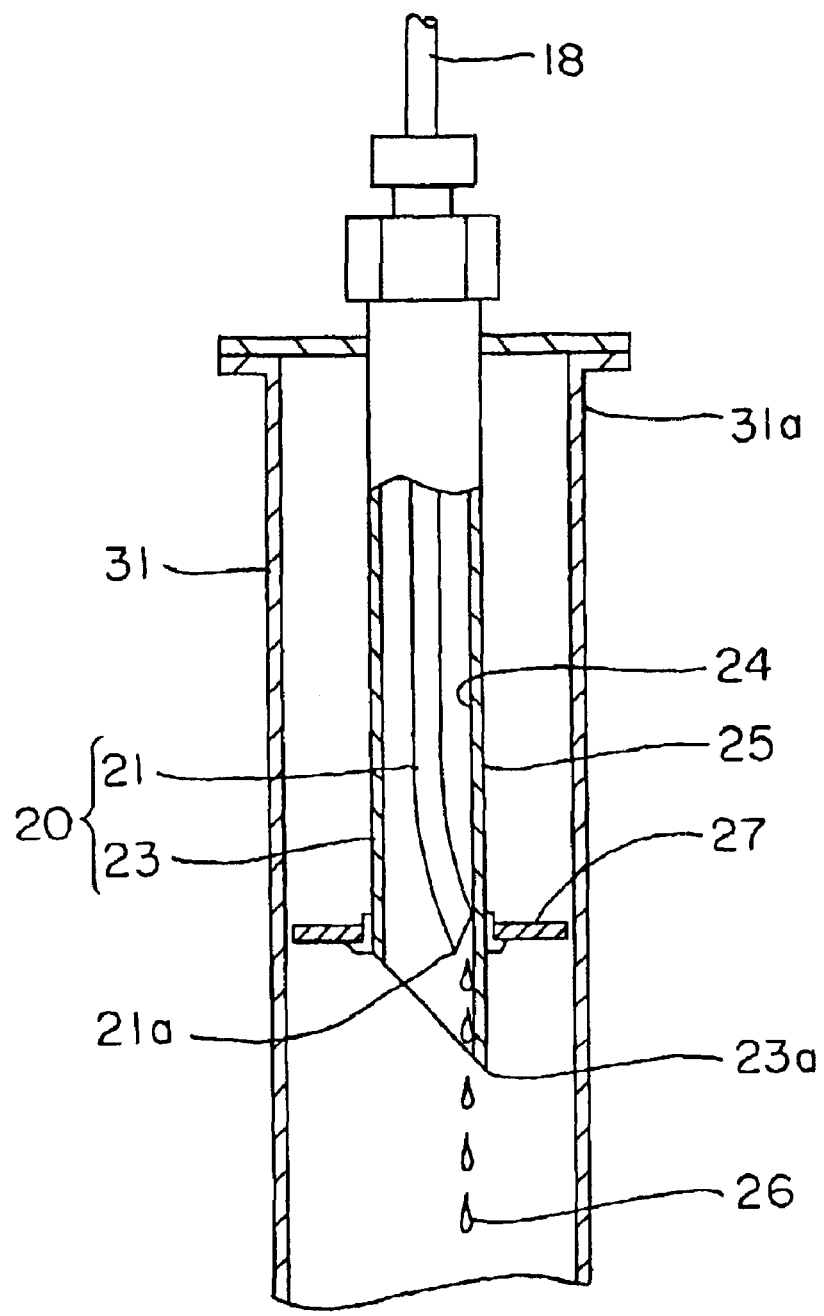
FIG. 4 is a vertical sectional view of the essential portion of a measuring apparatus according to another embodiment.
Figure 5:
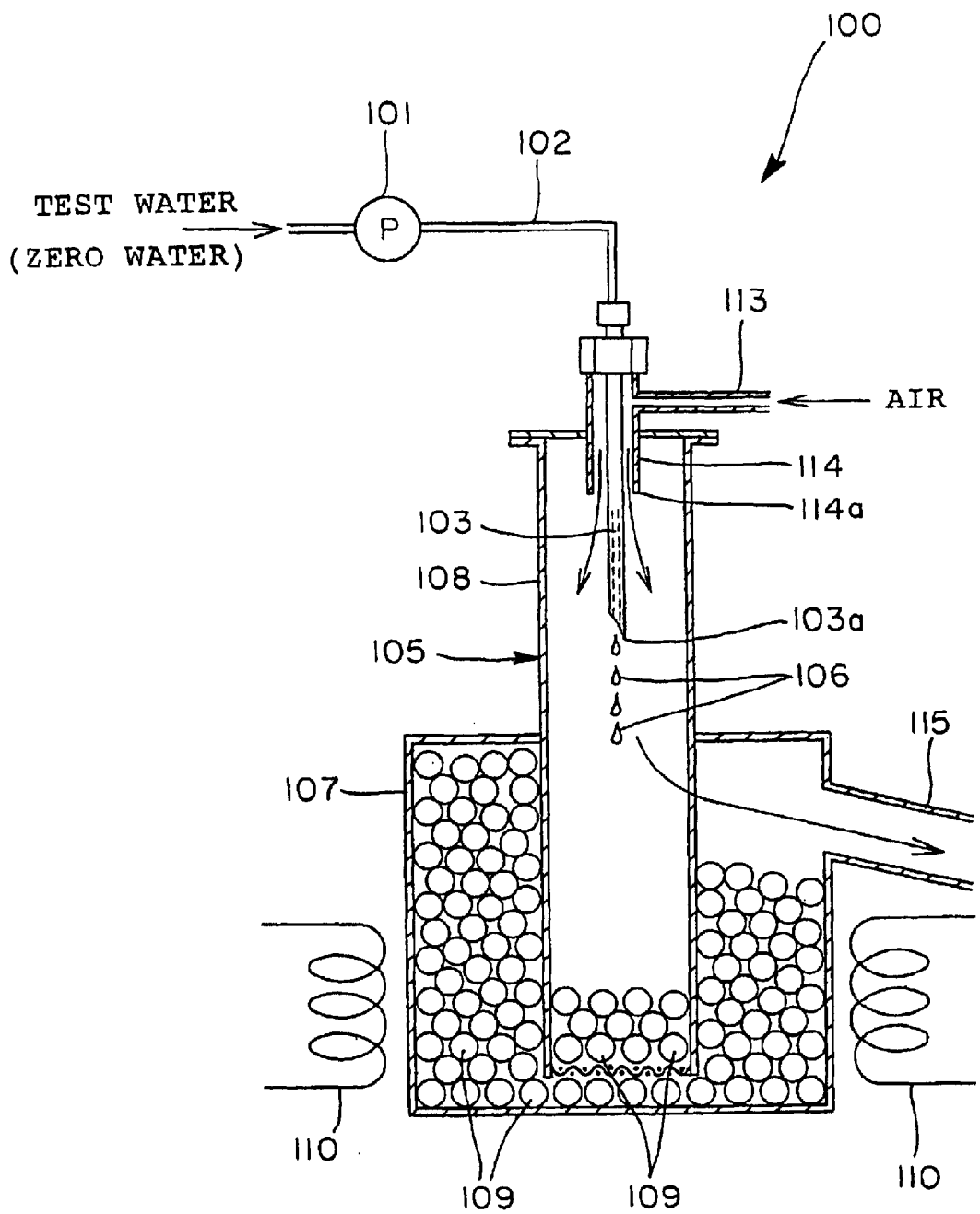
FIG. 5 is a vertical sectional view of the essential portion of a related-art carbon dioxide gas measuring apparatus.

FIG. 1 is a general schematic view of a measuring apparatus of a component contained in test water according to the invention, FIG. 2 is a vertical sectional view of a combustion furnace and a test water dropping unit of the measuring apparatus, FIG. 3 is a vertical sectional view of the essential portion of the measuring apparatus, FIG. 4 is a vertical sectional view of the essential portion of a measuring apparatus according to another embodiment, and FIG. 5 is a vertical sectional view of the essential portion of a related-art carbon dioxide gas measuring apparatus.

In a measuring apparatus 10 of a component contained in test water as shown in FIG. 1, test water is introduced into a first test water feed pipe 12 by a first feed pump 11, and hydrochloric acid is also introduced into the first test water feed pipe 12 from a hydrochloric acid tank 14 by a second feed pump 13. The test water and the hydrochloric acid introduced into this first test water supply pipe 12 are made to flow into an inorganic carbon removing tank 15, and at the same time, air is made to flow into the inorganic carbon removing tank 15 from an air feed pipe 16. After inorganic carbon has been removed from the test water in the inorganic carbon removing tank 15, the test water is introduced into a test water dropping unit 20 via a second test water feed pipe (a test water feed pipe) 18 by a third feed pump 17 and the test water is dropped into a combustion furnace 30 from the tip of the test water dropping unit 20, and the test water dropped into the combustion furnace 30 is combusted in the combustion furnace 30.

Gases generated by combustion are introduced into a gas inlet pipe 41 via a gas introducing pipe 40 by means of carrier air introduced into the interior of the combustion furnace 30 through a test water dropping nozzle 21. The gases are introduced into an infrared analyzer 45 via a condenser 42, an electronic cooler 43 and a filter 44, and the concentration of carbon dioxide gas contained in the gases is measured by the infrared analyzer 45, and the measured result is outputted as a signal.

The test water dropping unit 20 and the combustion furnace 30 of this measuring apparatus 10 will be described below in detail with reference to FIGS. 2 to 4.

As shown in FIG. 2, the combustion furnace 30 is provided with a combustion furnace body 31 formed in a cylindrical shape, and the test water dropping nozzle 21 is disposed at a top end 31a of the combustion furnace body 31, while a reactor 32 is provided at a bottom 31b of the combustion furnace body 31. A bottom opening 31c of the combustion furnace body 31 communicates with the reactor 32 via a mesh 33.

Alumina balls 35 (for example, 5.5 kg each) are accommodated as heat-accumulating balls at the bottom 31b of the combustion furnace body 31 and in the interior of the reactor 32, and a heater 36 is disposed at the periphery of the reactor 32.

Since the alumina balls 35 are accommodated as heat-accumulating balls in the interior of the reactor 32 and at the bottom 31b of the combustion furnace body 31, it is possible to increase the amount of heat accumulation in the interior of the reactor 32 and at the bottom 31a of the combustion furnace body 31. Accordingly, the temperature inside the reactor 32 and the temperature at the bottom 31b of the combustion furnace body 31 are not prevented from lowering when drops of the test water fall into the reactor 32, whereby the interior of the reactor 32 and the bottom 31a of the combustion furnace body 31 can be maintained at design temperatures.

Furthermore, since the combustion furnace 30 is formed of a special alloy called RA-333 (United States Standard ASTM B718 and United States Military Standard AMS 5717), the volume of the reactor 32 can be made, for example, as large as about 5.5 liters.

The volumes of existing combustion furnaces used generally are 200–300 milliliters. Therefore, as compared with such existing combustion furnaces, although the amount of test water measurable by the existing combustion furnaces is 1–50 µml/measurement, the combustion furnace 30 according to the invention enables the measurable amount of test water to be increased to 1–4 ml/measurement which is 20–4,000 times as large as the measurable amount of test water in the existing combustion furnaces, whereby the combustion furnace 30 can also measure test water which contains suspended solids.

As shown in FIGS. 2 and 3, in the test water dropping unit 20, the test water dropping nozzle 21 for dropping test water into the combustion furnace 30 is provided at the top end 31a of the combustion furnace 30 (i.e., the top end 31a of the combustion furnace body 31), and a protective pipe 23 is provided outside the test water dropping nozzle 21 so that the protective pipe 23 accommodates the test water dropping nozzle 21. A bottom end 23a of the protective pipe 23 is disposed to extend downward from the test water dropping nozzle 21 and is formed at an acute angle, and a tip 21a of the test water dropping nozzle 21 is disposed in abutment with an inner circumferential surface 24 of the protective pipe 23.

In this construction, as shown in FIG. 3, test water which drops from the tip 21a of the test water dropping nozzle 21 is guided to the inner circumferential surface 24 of the protective pipe 23, and the test water guided to the inner circumferential surface 24 is made to flow down to the bottom end 23a of the protective pipe 23. The test water is dropped as drops 26 from the bottom end 23a onto the alumina balls 35 in the combustion furnace 30, whereby the drops 26 can be completely combusted.

During this time, there is a case where the test water is combusted in the state of adhering to the bottom end 23a of the protective pipe 23. However, since the protective pipe 23 is formed to be comparatively thick so that the test water dropping nozzle 21 is accommodated in the protective pipe 23, the protective pipe 23 is not clogged up even if an evaporated residue adheres to the bottom end 23a of the protective pipe 23 as the result of combustion.

The second test water feed pipe 18 which communicates with the top end of the test water dropping nozzle 21 communicates with an air feed pipe 50 on the upstream side of the test water dropping nozzle 21. This air feed pipe 50 is provided with a check valve 51, a flow meter 52, a flow control valve 53 and a filter 54.

Accordingly, when air is fed to the air feed pipe 50 as indicated by an arrow, the air is introduced into the test water dropping nozzle 21 via the filter 54, the flow control valve 53, the flow meter 52 and the check valve 51, and is fed into the combustion furnace 30 from the tip 21a of the test water dropping nozzle 21.

In this manner, since the air is fed into the combustion furnace 30 through the test water dropping nozzle 21, the test water within the test water dropping nozzle 21 can be rapidly transported to the tip 21a of the test water dropping nozzle 21 by the air, and the test water can be efficiently guided from the tip 21a of the test water dropping nozzle 21 to the inner circumferential surface 24 of the protective pipe 23.

Accordingly, while the test water is being dropped into the combustion furnace 30, the test water can be dropped in the state of the small drops 26 as shown in FIG. 3. The drops 26 of the test water dropped in this manner can be efficiently completely combusted, whereby the amount of gas required for measurement of carbon dioxide gas can be reliably obtained in a short time.

Specifically, as described previously in connection with the related art, the existing carbon dioxide gas measuring apparatus has required 10–15 minutes to measure carbon dioxide gas, but the measuring apparatus 10 according to the invention can reduce its measurement time to 4–6 minutes.

In addition, a zero water feed pipe 56 for feeding zero water (for example, city water) communicates with the second test water feed pipe 18 on the downstream side of the third feed pump 17, and the zero water feed pipe 56 is provided with a zero water pump 57.

Accordingly, when the zero water pump 57 is driven, zero water can be introduced into the zero water feed pipe 56, and the zero water is further introduced into the second test water feed pipe 18 from the zero water feed pipe 56. Accordingly, the zero water is introduced into the test water dropping nozzle 21 via the second test water feed pipe 18, and this zero water can be dropped into the combustion furnace 30 from the tip 21a of the test water dropping nozzle 21.

Since the zero water feed pipe 56 communicates with the second test water feed pipe 18 in this manner, it is not necessary to pass zero water through the first test water supply pipe 12 and the second test water feed pipe 18 when the test water dropping nozzle 21 and the protective pipe 23 are to be cleaned or zero-point adjustment (initial-value setting) is to be performed on the measuring apparatus.

Accordingly, it is not necessary to make zero water flow through a flow passage for a time longer than necessary, whereby it is possible to shorten the time required to clean the test water dropping nozzle 21 and the protective pipe 23 and the time required for the zero-point adjustment (initial-value setting) of the measuring apparatus.

In the invention, a disk-shaped separating member 27 for separating the upper and lower portions of the combustion furnace 30 from each other can be fitted at a location near the bottom end 23a of an outer circumferential wall 25 of the protective pipe 23 as shown in FIG. 4. By fitting this separating member 27, it is possible to separate a portion of lower temperature in the combustion furnace 30 (a portion near the top of the combustion furnace 30) from a portion of higher temperature in the combustion furnace 30 (a portion near the bottom of the combustion furnace 30), whereby temperature nonuniformity is reduced in the combustion furnace 30 and the drops 26 of test water can be efficiently combusted. It is, therefore, possible to eliminate nonuniformity in the status of generation of carbon dioxide gas due to combustion nonuniformity as well as the dispersion of measured values of the measuring apparatus.

This separating member 27 may be made of any kind of material such as stainless steel, inconel, platinum or quartz, and can be easily fitted by spring pins or the like.

The separating member 27 is preferably a thin plate of approximately 1–2 mm thick, and by forming the separating member 27 into such a thin plate, it is possible to achieve the effect of preventing high temperatures from being transmitted to the test water dropping nozzle 21.

The test water dropping nozzle 21 is a nozzle made of polytetrafluoroethylene superior in water repellency, and can reliably drain test water off the tip 21a of the test water dropping nozzle 21 to prevent test water from adhering to the tip 21a of the test water dropping nozzle 21.

Accordingly, while the drops 26 of test water are being combusted, an evaporated residue is prevented from adhering to the tip 21a of the test water dropping nozzle 21, whereby the tip 21a of the test water dropping nozzle 21 can be prevented from being clogged up.

In addition, since the protective pipe 23 is a tube made of quartz glass superior in heat resistance, even if the protective pipe 23 is heated at high temperatures in the combustion furnace 30, for example, the bottom end 23a of the protective pipe 23 is not melted by heat, whereby test water can be efficiently dropped from the bottom end 23a of the protective pipe 23. Accordingly, test water can be efficiently fed into the combustion furnace 30.

Furthermore, in the case where a chemiluminescent type of nitrometer is used instead of the infrared analyzer 45, the measuring apparatus can also be used as a total nitrometer (because a large amount of test water can be obtained to achieve a concentration sufficient for measurement).

The preferred embodiment has been described above with reference to the example in which the measuring apparatus 10 is provided with the hydrochloric acid tank 14 and the inorganic carbon removing tank 15 for removing inorganic carbon from hydrochloric acid, and measures the concentration of carbon dioxide gas from which inorganic carbon is removed by passing test water through the hydrochloric acid tank 14 and the inorganic carbon removing tank 15. However, the invention is not limited to this example, and can also be applied to a measuring apparatus which is not provided with the hydrochloric acid tank 14 nor the inorganic carbon removing tank 15 and measures the concentration of carbon dioxide gas from which inorganic carbon is not removed.

As is apparent from the foregoing description, in the measuring apparatus of a component according to the invention, a protective tube is provided outside a test water dropping nozzle to protect the test water dropping nozzle, and the tip of the protective pipe is extended downward from the test water dropping nozzle and the tip of the test water dropping nozzle is brought into abutment with the inner circumferential surface of the protective pipe.

Accordingly, test water dropped from the tip of the test water dropping nozzle is guided to the inner circumferential surface of the protective tube. The test water guided to the inner circumferential surface is made to flow down to the tip of the protective pipe, and is dropped from the tip into the combustion furnace and is combusted therein.

At this time, the drops are combusted with the test water adhering to the tip of the protective pipe, but since the protective pipe is formed to be comparatively thick so that the test water dropping nozzle is accommodated in the protective pipe, the protective pipe is not clogged up even if an evaporated residue in the test water adheres to the inner circumferential surface of the tip of the protective pipe as the result of the combustion of the test water.

Accordingly, the measuring apparatus can prevent the protective pipe from being clogged up and suitably feed the test water into the combustion furnace, and therefore, has the advantage of highly accurately measuring carbon dioxide gas contained in the test water.

Accordingly, the measuring apparatus can efficiently completely combust an inorganic substance contained in the drops of the test water, so that the inorganic substance can be changed to 100% carbon dioxide gas and a maximum concentration of carbon dioxide gas can be transported to an infrared analyzer in a comparatively short time. The measuring apparatus has, therefore, the advantage of achieving accurate measurement in a short time.

In the measuring apparatus of a component according to the invention, owing to the presence of a separating member, temperature nonuniformity in the combustion furnace is reduced and the drops of test water can be efficiently combusted. Accordingly, the measuring apparatus has the advantage of eliminating nonuniformity in the status of generation of carbon dioxide gas due to combustion non-uniformity as well as the dispersion of measured values of the measuring apparatus.

In the measuring apparatus of a component according to the invention, air is fed into the combustion furnace through the test water dropping nozzle, whereby test water within the test water dropping nozzle can be rapidly transported to the tip of the test water dropping nozzle by the air. Accordingly, the test water can be efficiently guided from the tip of the test water dropping nozzle to the inner circumferential surface of the protective pipe, and while the test water is being dropped into the combustion furnace, the test water can be dropped in the form of small drops.

Accordingly, the drops of test water can be efficiently completely combusted and the amount of gas required for measurement of carbon dioxide gas can be reliably obtained in a short time. The measuring apparatus has, therefore, the advantage of highly accurately measuring carbon dioxide gas contained in test water.

In the component measuring apparatus of a component according to the invention, the test water dropping nozzle is formed of polytetrafluoroethylene. Polytetrafluoroethylene is superior in water repellency and can reliably drain test water off the tip of the test water dropping nozzle to prevent test water from adhering to the tip of the test water dropping nozzle.

Accordingly, the measuring apparatus has the advantage that while the drops of test water are being combusted, an evaporated residue can be prevented from adhering to the tip of the test water dropping nozzle, whereby the tip of the test water dropping nozzle can be prevented from being clogged up.

In addition, since the protective pipe can be prevented from being clogged up, test water can be suitably fed into the combustion furnace, so that carbon dioxide gas in test water can be accurately measured.

In addition, the protective pipe is formed of quartz glass, and since this quartz glass is superior in heat resistance, even if the protective pipe is heated at high temperatures in the combustion furnace, for example, the bottom end of the protective pipe can be prevented from being melted by heat, whereby test water can be efficiently dropped from the bottom end of the protective pipe. Accordingly, test water can be efficiently fed into the combustion furnace.

Accordingly, the measuring apparatus has the advantage that since test water can be efficiently fed into the combustion furnace, the carbon dioxide gas contained in the test water can be accurately measured.

In the measuring apparatus of a component according to the invention, since a zero water feed pipe communicates with a test water feed pipe, a dedicated flow passage through which zero water is made to flow can be obtained. Accordingly, the measuring apparatus has the advantage that since the length of the zero water feed pipe can be made short, it is possible to shorten the time required to clean the test water dropping nozzle and the protective pipe and the time required for the zero-point adjustment (initial-value setting) of the measuring apparatus.

What is claimed is:

1. An apparatus for determining the nature of at least one liquid organic compound by analyzing an outlet gas, which is a combustion product of said at least one liquid organic compound, said apparatus comprising:

means for mixing said at least one liquid organic compound with water to form a liquid mixture of said at least one liquid organic compound and water;

a combustion furnace for combusting said at least one organic compound in said liquid mixture of at least one organic compound and water, said combustion furnace having an upper section and a lower section;

a liquid test sample inlet nozzle to said combustion furnace, through which said liquid mixture of said at least one liquid organic compound and water is introduced into said combustion furnace;

means for introducing an oxygen-containing gas into said combustion furnace; and a protective pipe, positioned around an outside of said liquid test sample inlet nozzle, such that a tip of said liquid test sample inlet nozzle is in abutting communication with an inner circumferential surface of said protective pipe, said protective pipe having a tip extending from said liquid test sample inlet nozzle at an acute angle thereto.

2. The apparatus according to claim 1, further comprising a separator, positioned at a lower end of an outer circumferential wall of said protective pipe, for separating said upper and said lower sections of said combustion furnace.

3. The apparatus according to claim 1, wherein said means for introducing an oxygen-containing gas into said combustion furnace is said liquid test sample inlet nozzle.

4. The apparatus according to claim 1, wherein said liquid test sample inlet nozzle is made of polytetrafluoroethylene, and said protective pipe is made of quartz glass.

5. The apparatus according to claim 1, further comprising a pure water inlet nozzle, in communication with said liquid test sample inlet nozzle, for introducing pure water for washing said liquid test sample inlet nozzle, and for providing a pure water reference sample for calibrating apparatus for analyzing said outlet gas.

* * * * *